United States Patent [19]

Shiokawa et al.

[11] Patent Number: 5,231,098
[45] Date of Patent: Jul. 27, 1993

[54] INSECTICIDAL NITRO-SUBSTITUTED HETEROCYCLIC COMPOUNDS

[75] Inventors: Kozo Shiokawa, Kanagawa; Shinichi Tsuboi, Tokyo; Shoko Sasaki, Tokyo; Koichi Moriya, Tokyo; Yumi Hattori, Tokyo; Katsuhiko Shibuya, Tokyo, all of Japan

[73] Assignee: Nihon Bayer Agrochem K.K., Tokyo, Japan

[21] Appl. No.: 823,240

[22] Filed: Jan. 21, 1992

Related U.S. Application Data

[62] Division of Ser. No. 699,068, May 13, 1991, Pat. No. 5,122,527, which is a division of Ser. No. 510,509, Apr. 18, 1990, Pat. No. 5,036,082, which is a division of Ser. No. 353,370, May 17, 1989, Pat. No. 4,960,780, which is a division of Ser. No. 208,421, Jun. 17, 1988, Pat. No. 4,876,263.

[30] Foreign Application Priority Data

Jun. 26, 1987 [JP] Japan .................. 62-157528

[51] Int. Cl.$^5$ .................. A61K 31/505; C07D 487/04
[52] U.S. Cl. .................. 514/258; 544/279
[58] Field of Search .................. 544/279; 514/258

[56] References Cited

FOREIGN PATENT DOCUMENTS 3638121 12/1987 Fed. Rep. of Germany .

OTHER PUBLICATIONS

Solervay et al., Adv. in Pesticide Science, Part 2, Pergamon Press, pp. 206-207 (1978).

Schroeder et al., Pesticide Biochem. and Physiology, vol. 2, pp. 148-160 (1984).

Primary Examiner—Bernard Dentz
Attorney, Agent, or Firm—Sprung Horn Kramer & Woods

[57] ABSTRACT

Nitro-substituted heterocyclic compounds of the formula (I)

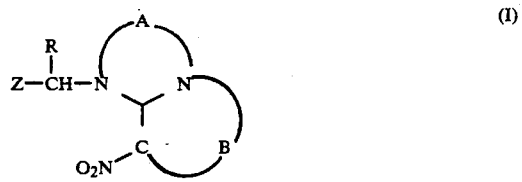

wherein R is hydrogen or alkyl,
Z is an optionally substituted aryl or optionally substituted heterocyclic groun containing at least one atom selected from N, O and S,
A is optionally substituted ethylene or optionally substituted trimethylene, and
B stands for 2 or 3 members of a heterocyclic ring which is formed, together with the adjacent C-atom and N-atom and at least one of said members may represent a hetero atom and may be optionally substituted, provided that when B stands for 3 members, two of which are carbon atoms and the other one is a nitrogen atom which is located in the middle of the three members, then at least one of said two carbon atoms must be substituted by a keto group. Such compounds being useful as insecticides.

4 Claims, No Drawings

INSECTICIDAL NITRO-SUBSTITUTED HETEROCYCLIC COMPOUNDS

This is a division of application Ser. No. 07/699,068, filed May 13, 1991, now U.S. Pat. No. 5,122,527 which is a division of application Ser. No. 510,509 filed Apr. 18, 1990, now U.S. Pat. No. 5,036,082; which is a division of application Ser. No. 353,370 filed May 17, 1989 now U.S. Pat. No. 4,960,780; which is a division of application Ser. No. 208,421 filed Jun. 17, 1988, now U.S. Pat. No. 4,876,263.

The present invention relates to novel nitro-substituted heterocyclic compounds, to processes for their preparation and to their use as insecticides.

The following nitro-substituted heterocyclic compounds of the formulae (A) to (E) have already been disclosed in literature:

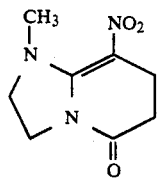
(A)

(see Chemische Berichte, 1968, Vol. 119, pp. 2208-2219)

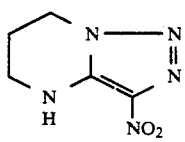
(B)

(see J. Chem, Soc., Perkin Transaction I, 1979, pp. 2361-2363),

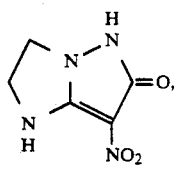
(C)

(D)

(see J. Heterocycl. Chem., 1980, vol. 17, p 1413)

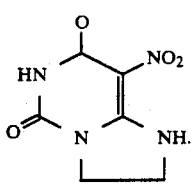
(E)

(see Heterocycles, 1980, vol. 15, p 437)

There have now been found novel nitro-substituted heterocyclic compounds of the formula (I):

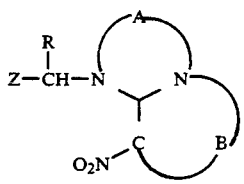
(I)

wherein R is hydrogen or alkyl,
Z is an optionally substituted aryl or optionally substituted heterocyclic group containing at least one atom selected from N, O and S,
A is optionally substituted ethylene or optionally substituted trimethylene radical, and
B stands for 2 or 3 members of a heterocyclic ring which is formed, together with the adjacent C-atom and N-atom and at least one of said members may represent a hetero atom and may be optionally substituted, provided that when B stands for 3 members, two of which are carbon atoms and the other one is a nitrogen atom which is located in the middle of the three members, then at least one of said two carbon atoms must be substituted by a keto group.

The compounds of the formula (I) can be obtained by a process in which
a) compounds of the formula (II)

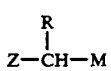
(II)

wherein R and Z respectively have the same meanings as above, M represents halogen, or —OSO$_2$—L in which L denotes alkyl or aryl which may be substituted, are reacted with compounds of the formula (III);

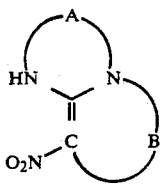
(III)

wherein A and B are as defined above, in the presence of inert solvents and, if appropriate, in the presence of a base, or b) [When B in the formula (I) is

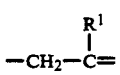

(wherein R$^1$ is alkyl or aryl),

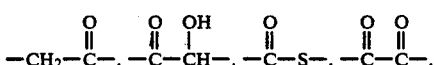

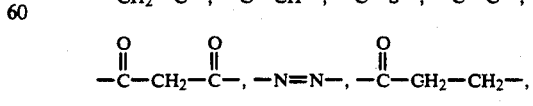

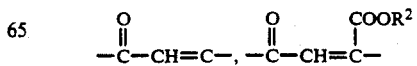

(wherein R$^2$ is alkyl),

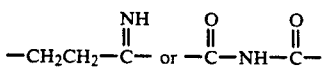

(the symbol "+" denotes a linkage between B and the adjacent nitrogen atom), then B is replaced with B'.]
compounds of the formula (IV)

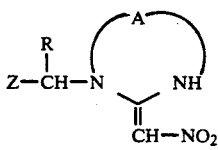

wherein R, Z and A are the same as above, are reacted with compounds represented by the following formula (V)

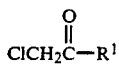

wherein $R^1$ is the same as above,
glyoxal represented by the following formula (VI),

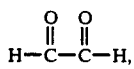

glyoxylic acid represented by the following formula (VII),

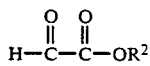

wherein $R^2$ is the same as above,
chlorothioformyl chloride represented by the following formula (VIII),

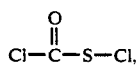

oxalyl chloride represented by the following formula (IX),

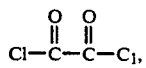

malonyl chloride represented by the following formula (X),

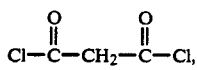

4-chlorobenzene-sulfonylazide represented by the following formula (XI),

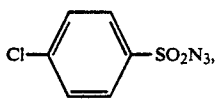

acrylic acid alkyl represented by the following formula (XII), $$CH_2=CH-COOR^2 \quad (XII)$$

wherein $R^2$ is the same as above,
propiolic acid alkyl represented by the following formula (XIII), $$CH\equiv CCOOR^2 \quad (XIII)$$

wherein $R^2$ is the same as above,
acetylene dicarboxylic acid dialkyl represented by the following formula (XIV), $$R^2OOCC\equiv CCOOR^2 \quad (XIV)$$

wherein $R^2$ is the same as above,
halopropionitrile represented by the following formula (XV), $$Hal-CH_2CH_2CN \quad (XV)$$

wherein Hal is a halogen atom, or
chlorocarbonyl isocyanate represented by the following formula (XVI),

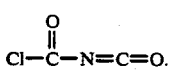

The nitro-substituted heterocyclic compounds of the formula (I) according to the present invention exhibit strong insecticidal activities.

It is moreover surprising that the nitro-substituted heterocyclic compounds of the formula (I) according to the present invention exhibit considerably improved insecticidal activities as compared with the known compounds having analogous structures to the present compounds according to the invention.

Among the nitro-substituted heterocyclic compounds according to the invention, of the formula (I), preferred compounds are those in which R is hydrogen or $C_1$-$C_4$ alkyl, Z is $C_6$-$C_{10}$ aryl, or a 5 to 6-membered heterocyclic group containing 1 to 2 hetero atoms selected from the group consisting of O, S and N, at least one of which is a nitrogen atom, and said aryl and heterocyclic group may be substituted respectively by any one member optionally selected from the group consisting of halogen, $C_1$-$C_4$ alkyl, $C_1$-$C_4$ alkoxy, $C_1$-$C_4$ haloalkyl, $C_1$-$C_4$ alkylthio, $C_1$-$C_4$ haloalkoxy, $C_1$-$C_4$ haloalkylthio, nitro, and cyano, A is ethylene or trimethylene, both of which may be substituted by methyl, and B stands for 2 or 3 members of a heterocyclic ring which is formed, together with the adjacent C-atom and N-atom, and at least one of said members may represent a nitrogen atom or a sulfur atom and may be optionally substituted by at least one selected from the group consisting of halogen, $C_1$-$C_6$ alkyl, $C_1$-$C_4$ alkoxy, alkoxycarbonyl having 1 to 4 carbon atoms in the alkoxy part, optionally substituted $C_6$-$C_{10}$ aryl, keto, imino, phenoxy, $C_1$-$C_4$ alkoxythio, alkoxycarbonylimino having 1 to 4 carbon atoms in the alkoxy part, phenoxycarbonylimino, benzoylimino, benzyl, cyano, thioketo, benzyl, hydroxy and $C_1$-$C_2$ alkylidene, provided that where B stands for 3 members, two of which are carbon atoms and the other of which is a nitrogen atom which is located in the middle of the three members, then at least one of said two carbon atoms is substituted by a keto group.

Very particularly preferred nitro-substituted heterocyclic compounds of the formula (I) are those in which R is hydrogen, or methyl, Z is phenyl, or a 5 to 6-membered heterocyclic group containing 1 to 2 hetero atoms selected from the group consisting of O, S and N, at least one of which is a nitrogen atom, and said phenyl and heterocyclic group may be optionally substituted by one or two selected optionally from the group consisting of fluorine, chlorine, bromine, methyl, ethyl, methoxy, trifluoromethyl, methylthio, trifluoromethoxy, trifluoromethylthio, nitro and cyano, A is ethylene or trimethylene, both of which may be substituted by methyl, and B stands for 2 or 3 members of a heterocyclic ring which is formed, together with the adjacent C-atom and N-atom and at least one of said members may represent a nitrogen atom or a sulfur atom and may be optionally substituted by at least one substituent selected from the group consisting of fluorine, chlorine, bromine, methyl, methoxy, alkoxycarbonyl having 1 to 2 carbon atoms in the alkoxy part, phenyl, keto, imino, phenoxy, alkoxycarbonyl-imino having 1 to 2 carbon atoms in the alkoxy part, phenoxycarbonyl-imino, benzoyl imino, benzyl, cyano, thioketo, benzyl, hydroxy, and $C_1$-$C_2$ alkylidene, provided that where B stands for 3 members, two of which are carbon atoms and the other one is a nitrogen atom which is located in the middle of the three members, then at least one of said two carbon atoms must be substituted by a keto group.

As individual examples of the compounds of the formula (I) according to the invention, the following compounds can be mentioned:

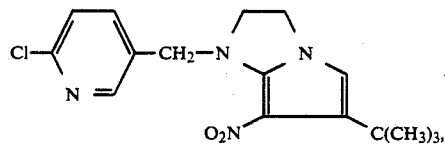

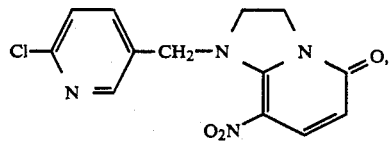

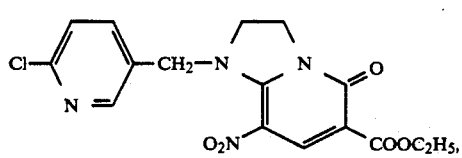

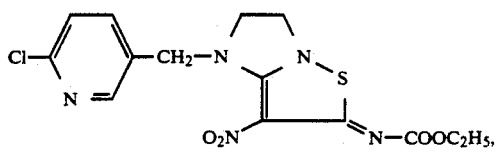

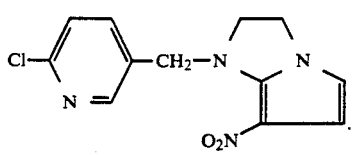

In the above-mentioned process a), if use is made, as starting compounds, for example, of 2-chloro-5-chloromethylpyridine, and ethyl-1,2,3,5-tetrahydro-8-nitro-imidazo[1,2-a]pyridin-5-one-6-carboxylate, the reaction proceeds as follows;

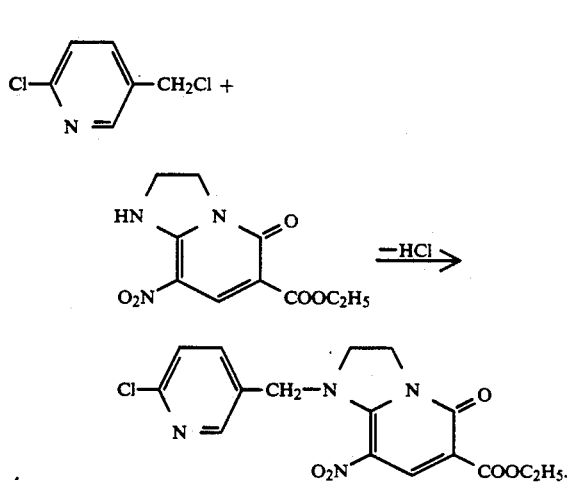

In the above-mentioned process b), if use is made, as starting compounds, for example, of 2-nitromethylene-3-(2-chloro-5-pyridylmethyl)imidazolidine and propiolic acid methyl ester, the reaction proceeds as follows;

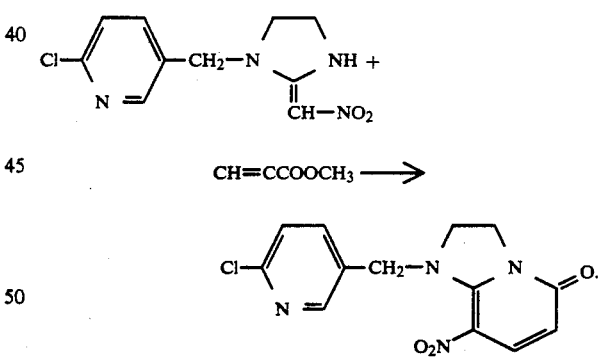

In the compounds of the formula (II) in the above-mentioned process a), R, Z and M have the same meanings as defined above.

In the formula (II), R and Z preferably have the preferred meanings respectively as indicated above, M is chlorine or tosyloxy.

The compounds of the formula (II) are already known in the art from, for example, Japanese Patent Laid-open No. 81382/1987, and as individual examples may be mentioned 2-chloro-5-chloromethylpyridine, and 2-chloro-5-chloromethylthiazole.

In the compounds of the formula (III) in the process a), A and B have the same meanings as defined above.

In the formula (III), A and B preferably have respectively the preferred meanings as indicated above.

The compounds of the formula (III) include known ones described, for example, in "Journal of Chemical Society Perkin" I, 1979, p. 2361, "Journal of Heterocyclic Chemistry", Vol. 17, p. 1413, and "Chemische Berichte", Vol. 119, p. 2208.

A part of the compounds of the formula (III) can be obtained by reacting the compounds represented by the following formula (XVII)

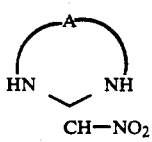  (XVII)

wherein A has the same meaning as defined above, with compounds having the above-mentioned formulae (V), (VI) (VII), (VIII), (IX), (X), (XI), (XII), (XIII), (XIV), (XV) or (XVI), according to process b).

The compounds of the above formula (XVII) are already known, for example, from Japanese Patent Laid-open No. 218,386/1985 and as individual examples thereof can be mentioned, 2-nitromethylene-imidazolidine, and 2-nitromethylene-tetrahydropyrimidine.

Moreover, each of the compounds of the formulae (V), (VI), (VII), (VIII), (IX), (X), (XI), (XII), (XIII), (XIV), (XV) and (XVI) are well-known in the field of the organic chemistry.

Further, the compound represented, for example, by the following formula (XVIII), which corresponds to the formula (III);

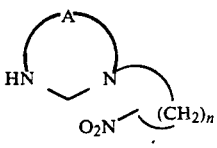  (XVII)

wherein A is the same as above, n is 2 or 3, can be obtained by decomposing, by an acid, the compounds represented by the following formula (XIX)

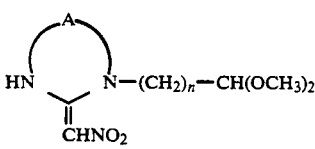  (XIX)

wherein A and n are the same as above, and subsequently cyclizing the product.

And the compounds of the above formula (XIX) can be obtained by reacting the compound represented by the formula (XX),

  (XX)

$H_2N-A-NH-(CH_2)_n-CH(OCH_3)_2$  (XX)

wherein A and n are the same as above, with 1-nitro-2,2-bis(methylthio)ethylene.

The compounds of the above formula (XX) can be obtained by reacting the compounds represented by the following formula (XXI),

$H_2N-A-NH_2$  (XXI)

wherein A is the same as above, with the compounds represented by the following formula (XXII),

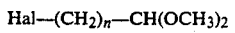
$Hal-(CH_2)_n-CH(OCH_3)_2$  (XXII)

wherein n is the same as above, Hal is a halogen atom.

Both compounds of the above formulae (XXI) and (XXII) are known compounds.

In the compounds of the formula (IV) in the process b↓, R, Z and A have respectively the same meanings as defined above.

In the formula (IV), R, Z and A preferably have respectively the preferred meanings as mentioned above.

The compounds of the formula (IV) are already known, for example, from Japanese Patent Laid-open Nos. 218,386/1985 and 183,271/1986, and as concrete examples of the compounds can be mentioned, for example, 1-(2-chloro-5-pyridylmethyl)-2-nitromethyleneimidazolidine,
1-(2-chloro-5-pyridylmethyl)-2-nitromethylenetetrahydropyrimidine,
1-(2-chloro-5-thiazolylmethyl)-2-nitromethyleneimidazolidine,
1-(2-fluoro-5-pyridylmethyl)-2-nitromethyleneimidazolidine, and
1-(2-methyl-5-pyridylmethyl)-2-nitromethyleneimidazolidine.

In carrying out the process a) mentioned above, use may be made, as suitable diluent, of any inert solvents.

Examples of the solvents or diluents are water; aliphatic, cycloaliphatic and aromatic, optionally chlorinated, hydrocarbons, such as hexane, cyclohexane, petroleum ether, ligroin, benzene, toluene, xylene, methylene chloride, chloroform, carbon tetrachloride, ethylene chloride, trichloroethylene, chlorobenzene and the like; ethers such as diethyl ether, methyl ethyl ether, di-isopropyl ether, dibutyl ether, propylene oxide, dioxane, tetrahydrofuran and the like; nitriles such as acetonitrile, propionitrile, acrylonitrile and the like; alcohols such as methanol, ethanol, iso-propanol, butanol, ethylene glycol and the like; acid amides such as dimethyl formamide, dimethyl acetamide and the like; and sulfones and sulfoxides such as dimethyl sulfoxide, sulfolane and the like; bases, for example, hydrides such as sodium hydride, potassium hydrides, alkali metal hydroxides, carbonates and tertiary amines such as triethylamine.

In the above-mentioned process a), the reaction temperature can be varied within a wide range. In general, the reaction is carried out at a temperature of about 0° to 100° C., preferably about 10°-80° C.

In general, the reaction is allowed to proceed under normal pressure, although it is also possible to employ a higher or lower pressure.

When the above-mentioned process a) according to the invention is carried out, use is made, for instance, of about 1.1 to 1.2 moles of sodium hydride as a base, and about 1 to 1.2 moles, preferably about 1 to 1.1 moles of the compounds of the formula (II) per 1 mole of the compounds of the formula (III). The reaction may be conducted in the presence of an inert solvent such as dimethyl sulfoxide, for example, to obtain the aimed compound.

When the above-mentioned process b) is carried out, it is possible to employ whatever inert solvent similar to that used in the process a) according to the invention.

The above-mentioned process b) can be carried out at reaction temperature varying within a wide range, for example, between about 0° C. and a boiling point of a mixture, preferably between about 0° C. and about 100° C.

The reaction is preferably carried out under normal pressure, although it is also possible to employ a higher or lower pressure.

In the process b), the reaction of the compounds of the formula (IV) either with the compounds of the formula (VI) or with the compounds of the formula (VII) can be conducted in the similar manner to the reactions described in U.S. Pat. No. 4,033,954 and U.S. Pat. No. 4,033,955.

Further, the reaction of the compounds of the formula (IV) either with the compounds of the formula (IX) or with the compounds of the formula (X) can be conducted according to the reaction similar to that described in "Journal für Praktische Chemie", Vol. 319, p. 149.

The reaction of the compounds of the formula (IV) with the compounds of the formula (XII), or with the compous of the formula (XIII), or with the compounds of the formula (XIV) can be carried out according to the commonly known Michael reaction.

The reaction of the compound having the formula (IV) with the compound having the formula (XV) is carried out in the presence of a base to give the desired nitro-substituted heterocyclic compound having the formula (Ia).

In the case where the formula (I) of the present invention is represented by the following formula (Ib),

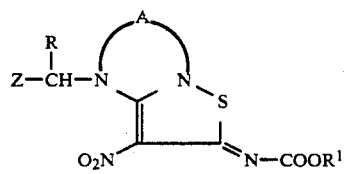

(Ib)

wherein R, Z, Z, and $R^1$ are the same as above, said compounds can be obtained, separately from the above-mentioned processes a) and b), by reacting the compounds of the formula (IV) with the compounds represented by the following formula (XXIII),

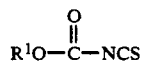

(XXIII)

wherein $R^1$ is the same as above, and subsequently reacting the reaction product with bromine.

The above reaction can be carried out according to the processes described in publications of "Tetrahedron", Vol. 33, p. 1057, the same, Vol. 37, p. 1470, and "Indian Journal of Chemistry", 15B, p. 886.

Further, if the compounds of the above formula (Ib) are hydrolyzed gently, the following compounds of the formula (Ic) which correspond to the formula (I) of the present invention can be obtained

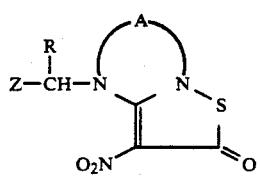

(Ic)

wherein R, Z and A are the same as above.

In the above-mentioned reaction wherein the compounds of the formula (IV) are reacted with the compounds of the formula (XXIII), and subsequently with bromine, if the reaction product, instead of being reacted with bromine, is heated in the presence of a catalytic amount of a base, then the following compounds of the formula (Id) which correspond to the formula (I) of the present invention can be obtained

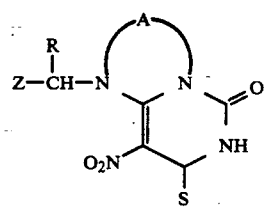

(Id)

wherein R, Z and A are the same as above.

If the compounds of the formula (I) of the present invention are represented by the following formula (Ie)

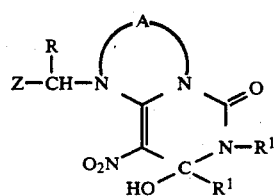

(Ie)

wherein R, Z, A and $R^1$ are the same as above, and $R^1$s are identical with or different from each other, the compounds of the formula (Ie) can be obtained by reacting the compounds of the following formula (XXIV)

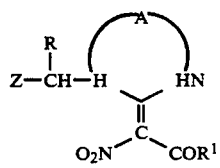

(XXIV)

wherein R, Z, A and $R^1$ are the same as above, with the compounds of the following formula (XXV),

$R^1$—NCO          (XXV)

wherein $R^1$ is the same as above, and the above reaction may be carried out according to the process described in U.S. Pat. No. 3,985,735.

Further, the compounds of the above formula (XXIV) are known ones described in Japanese Patent Laid-open No. 81382/1987, and it can be obtained according to the process described in the same.

The active compounds are well tolerated by plants, have a favorable level of toxicity to warm-blooded animals, and can be used for combating arthropod pests, especially insects which are encountered in agriculture, in forestry, in the protection of stored products and of materials, and in the hygiene field. They are active against normally sensitive and resistant species and against all or some stages of development. The above-mentioned pests include:

from the class of the Isopoda, for example Oniscus Asellus, *Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera; for example *Blatta orientalis, Periplaneta americana, Leucophaea maderae, Blattella germanica, Acheta domestica, Gryllotalpa* spp., *Locusta migrato ria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix*, Pemphigus spp., *Pediculus humanus corporis*, Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci,* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae*, Myzus spp., *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., Spodoptera exigua, Mamestra brassicae, Panolis flammea, Prodenia litura*, Spodoptera spp., *Trichoplusia ni, Carpocapsa pomonella*, Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae*, Diabrotica spp., *Psylliodes chrysocephala, Epilachna varivestis*, Atomaria spp., *Oryzaephilus surinamensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica;* from the order of the Hymenoptera for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa;*

Furthermore, in the field of veterinary medicine, the novel compounds of the present invention can effectively be employed for combating a variety of noxious animal-parasitic pests (internal- and external-parasitic pests), e.g. parasitic insects and nemotodes. Such animal-parasitic pests may be exemplified as follows:

From the class of Insecta, e.g. Gastrophilus spp., Stomoxys spp., Tricodectes spp., Rhodnius spp., *Ctenocephalides canis* and the like.

By the term "pesticides" herein is meant a substance which exhibits a combating action on pests including those illustrated above.

The active compounds can be converted into the customary formulations, such as solutions, emulsions, suspensions, powders, foams, pastes, granules, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in a known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. If water is used as an extender, organic solvents can, for example, also be used as auxiliary solvents.

As liquid solvents diluents or carriers, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic hydrocarbons, such as cyclohexane or paraffins, for example, mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethyl-sulphoxide, as well as water.

By liquefied gaseous diluents or carriers liquids are meant which would be gaseous at normal temperature and under normal pressure, for example, aerosol propellants such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example, alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese boron, copper, cobalt, molybdenum and zinc.

The formulations in general contain from 0.1 to 95 percent by weight of active compound, preferably from 0.5 to 90 percent by weight.

The active compounds according to the invention can be present in their commercially available formulations and in the use forms, prepared from these formulations, as a mixture with other active compounds, such as insecticides, baits, sterilising agents, acaricides, nematicides, fungicides, growth-regulating substances or herbicides. The insecticides include, for example, phosphates, carbamates, carboxylates, chlorinated hydrocarbons, phenylureas, substances produced by microorganisms.

The active compounds according to the invention can furthermore be present in their commercially available formulations and in the use forms, prepared from these formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 100% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The invention will be further illustrated by way of examples. However, it should be noted that the scope of the invention is not limited only to to the scope of the examples.

EXAMPLES OF SYNTHESIS

EXAMPLE 1

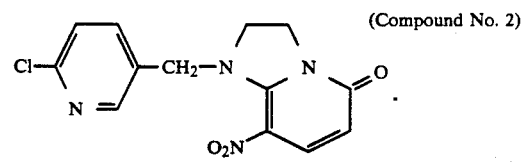

(Compound No. 2)

A mixed solution of 2-nitromethylene-3-(2-chloro-5-pyridylmethyl) imidazolidine (12.7 g), propiolic acid methylester (4.2 g) and methanol (100 ml) was refluxed under heating for about 20 hours. Subsequently methanol was distilled off under reduced pressure, and the residue was refined by a silica-gel column chromatography to give the desired 1,2,3,5-tetrahydro-1-(2-chloro-5-pyridylmethyl)-8-nitroimidazo[1,2-a] pyridin-5-one (8 g).

mp. 199°–203° C.

Example 2

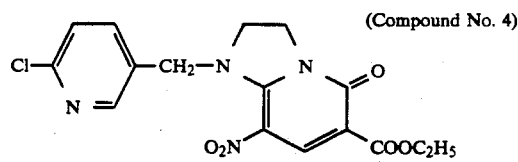

(Compound No. 4)

Ethyl-1,2,3,5-tetrahydro-8-nitro-5-oxaimidazo[1,2-a] pyridine-6-carboxylate (12.7 g) was dissolved in dry dimethyl-sulfoxide (60 ml), 60% sodium hydride (2 g) was added in small portions to the solution in a stream of nitrogen gas at room temperature, and then stirred at room temperature for an hour to obtain the sodium salt. Next, 2-chloro-5-chloromethylpyridine (8.1 g) was added thereto at room temperature, and the content was stirred at a room temperature for a day. The whole content was carefully poured out into 100 ml of ice cold water to deposit the desired compound as crystals, which were filtered off and washed with ethanol to give the desired ethyl-1,2,3,5-tetrahydro-1-(2-chloro-5-pyridimethyl)-8-nitro-imidazo[1,2-a]-5-one-6-carboxylate (12 g).

mp. 259°–263° C.

Example 3

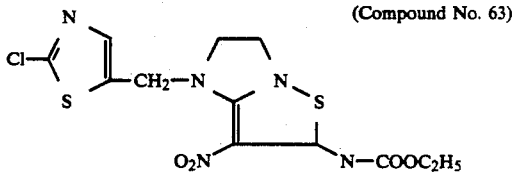

(Compound No. 63)

2-nitromethylene-3-(2-chloro-5-thiazolylmethyl)-imidazolidine (13 g) was suspended in dry acetonitrile (100 ml.). Ethoxycarbonylisothiocyanate (6.6 g) was added to the above mentioned suspension at room temperature, sucessively refluxed under heating for 10 minutes. The content was brough to room temperature, and subsequently stirred for an hour to deposit crystals, which were filtered off.

Next, the crystals were suspended in acetic acid (60 ml), while being stirred at a temperature of 10° C., and bromine (8 g) was added dropwise. When the dropping was completed, it was stirred further for an hour to complete the reaction. Acetic acid was distilled off under reduced pressure, water was added to the residue to dissolve it, sodium bicarbonate was added in small portions to the solution to make it alkaline, and it was subsequently extracted twice with dichloromethane. After the dichloromethane layer was dried with sodium sulfate, the solvent was distilled off, and the residue was recrystallized with ethanol to give the desired ethyl-2,4,5,6,-tetrahydro-4-(2-choro-5-thiazylmethyl-3-nitroimidazo[1,2-b]isothiazole-2-ylidenecarbamate (12 g).

Mp. 176°–180° C.

Compounds which can be prepared according to the same process as shown in the above Examples 1–3, together with the compounds of the Examples 1–3, are listed in the following Table 1.

TABLE 1

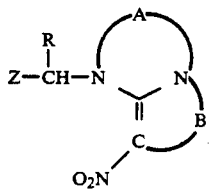

| Compound No. | Z | R | (Z—CH—N side) A | (C side) B (N side) | |
|---|---|---|---|---|---|
| 1 | Cl-pyridyl | H | —CH$_2$CH$_2$— | —CH$_2$CH$_2$C(=O)— | |
| 2 | Cl-pyridyl | H | —CH$_2$CH$_2$— | —CH=CHC(=O)— | mp. 199–203° C. |
| 3 | Cl-pyridyl | H | —CH$_2$CH$_2$— | —CH=CHC(COOCH$_3$)(=O)— | mp. 91–95° C. |
| 4 | Cl-pyridyl | H | —CH$_2$CH$_2$— | —CH=C(COOC$_2$H$_5$)—C(=O)— | mp. 259–263° C. |
| 5 | Cl-pyridyl | H | —CH$_2$CH$_2$— | —C(=O)—NH—C(=O)— | mp. 205–210° C. |
| 6 | Cl-pyridyl | H | —CH$_2$CH$_2$— | —C(=N—COOC$_2$H$_5$)—S— | mp. 131–135° C. (decomposition) |
| 7 | Cl-thiazolyl | H | —CH$_2$CH$_2$— | —CH=C(COOC$_2$H$_5$)—C(=O)— | mp. 256–260° C. |
| 8 | Cl-pyridyl | H | —CH$_2$CH$_2$— | —C(C(CH$_3$)$_3$)=CH— | mp. 148–150° C. |
| 9 | Cl-pyridyl | H | —CH$_2$CH$_2$— | —CH=CH— | mp. 139–143° C. |

TABLE 1-continued

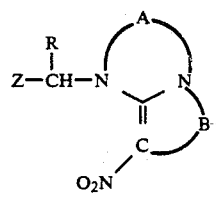

| Compound No. | Z | R | (Z—CH(R)—N side) A | (C side) B (N side) | |
|---|---|---|---|---|---|
| 10 | 6-chloro-3-pyridyl | H | —CH$_2$CH$_2$— | —C(=S)—NH—C(=O)— | mp. 233-237° C. (decomposition) |
| 11 | 3-pyridyl | H | —CH$_2$CH$_2$— | —CH$_2$CH$_2$— | |
| 12 | 6-chloro-3-pyridyl | H | —CH$_2$CH$_2$— | —CH$_2$CH$_2$— | |
| 13 | 6-chloro-3-pyridyl | H | —CH$_2$CH$_2$— | —C(CH$_3$)=CH— | |
| 14 | 6-fluoro-3-pyridyl | H | —(CH$_2$)$_3$— | —CH=CH— | |
| 15 | 6-methyl-3-pyridyl | H | —CH$_2$CH$_2$— | —CH=CH— | |
| 16 | 6-bromo-3-pyridyl | H | —CH$_2$CH$_2$— | —CH=CH— | |
| 17 | 5,6-dichloro-3-pyridyl | H | —CH$_2$CH$_2$— | —CH=CH— | |
| 18 | 6-chloro-3-pyridyl | H | —CH$_2$CH(CH$_3$)— | —CH=CH— | |
| 19 | 6-chloro-3-pyridyl | H | —(CH$_2$)$_3$— | —C(C(CH$_3$)$_3$)=CH— | |

TABLE 1-continued

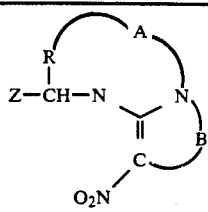

| Compound No. | Z | R | (Z—CH—N side) A | (C side) B (N side) |
|---|---|---|---|---|
| 20 | 2-chloro-5-pyridyl | H | —CH₂CH₂— | 4-Cl-C₆H₄—C=CH— |
| 21 | 2-chloro-5-pyridyl | H | —CH₂CH₂— | —C(C(CH₃)₃)=C(Br)— |
| 22 | 1-methyl-pyrazol-4-yl (H₃C—N—N) | H | —CH₂CH₂— | —CH=CH— |
| 23 | 1-ethyl-pyrazol-4-yl (H₃C₂—N—N) | H | —(CH₂)₃— | —CH=CH— |
| 24 | 3-methyl-isoxazol-5-yl (H₃C—, N—O) | H | —CH₂CH₂— | —CH=CH— |
| 25 | thiazol-2-yl | CH₃ | —CH₂CH₂— | —CH₂CH₂— |
| 26 | 2-chloro-thiazol-5-yl | H | —CH₂CH₂— | —CH=CH— |
| 27 | 2-chloro-thiazol-5-yl | H | —(CH₂)₃— | —C(CH₃)=CH— |
| 28 | 2-chloro-thiazol-5-yl | H | —CH₂CH₂— | —CCl=CH— |

TABLE 1-continued

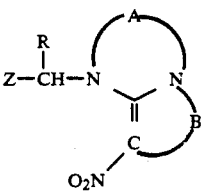

| Compound No. | Z | R | (Z—CH—N side) A | (C side) B (N side) |
|---|---|---|---|---|
| 29 | 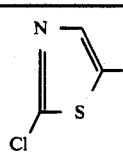 | H | —CH$_2$CH$_2$— | $\underset{\underset{}{-\text{C}=\text{CH}-}}{\text{OCH}_3}$ |
| 30 | 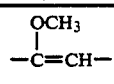 | H | —(CH$_2$)$_3$— | —CH=CH— |
| 31 | 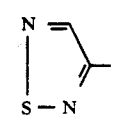 | H | —CH$_2$CH$_2$— | —CH=CH— |
| 32 |  | H | —(CH$_2$)$_3$— | —CH=CH— |
| 33 | 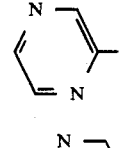 | H | —(CH$_2$)$_2$— | —CH=CH— |
| 34 | 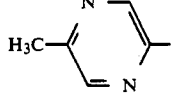 | H | —CH$_2$CH$_2$— | —CH$_2$CH$_2$— |
| 35 | 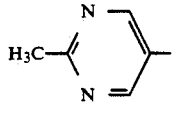 | H | —CH$_2$CH$_2$— | —CH=CH— |
| 36 | 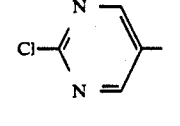 | H | —CH$_2$CH$_2$— | $\underset{\underset{}{-\text{C}=\text{CH}-}}{\text{COOC}_2\text{H}_5}$ |
| 37 | 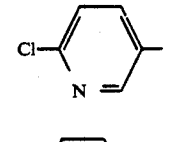 | H | —CH$_2$CH$_2$— | $-\text{CH}_2-\overset{\text{O}}{\overset{\|}{\text{C}}}-$ |
| 38 | 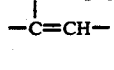 | H | —CH$_2$CH$_2$— | $-\text{CH}_2-\overset{\text{O}}{\overset{\|}{\text{C}}}-$ |
| 39 | 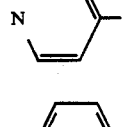 | CH$_3$ | —(CH$_2$)$_3$— | $-\text{CH}_2-\overset{\text{O}}{\overset{\|}{\text{C}}}-$ |

TABLE 1-continued

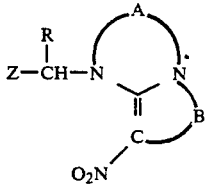

| Compound No. | Z | R | $\overset{R}{(Z-CH-N\text{ side})}$ A | (C side) B (N side) |
|---|---|---|---|---|
| 40 | 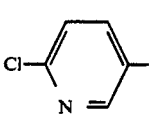 | H | —CH$_2$CH$_2$— | $\overset{CH_3}{-CH}\overset{O}{-C-}$ |
| 41 | 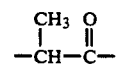 | H | —CH$_2$CH$_2$— | 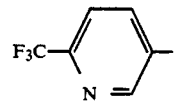 |
| 42 | 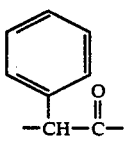 | H | —CH$_2$CH$_2$— | $-CH_2\overset{O}{-C-}$ |
| 43 | 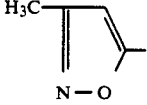 | H | —CH$_2$CH$_2$— | $-CH_2\overset{O}{-C-}$ |
| 44 | 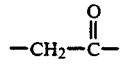 | H | —CH$_2$CH$_2$— | $-CH_2\overset{S}{-C-}$ |
| 45 | 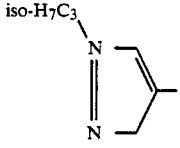 | H | —CH$_2$CH$_2$— | $-CH_2\overset{O}{-C-}$ |
| 46 | 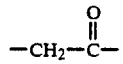 | H | $\overset{CH_3}{-CH_2CHCH_2-}$ | $-CH_2\overset{O}{-C-}$ |
| 47 | 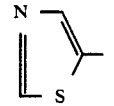 | H | —CH$_2$CH$_2$— | $\overset{OH}{-CH}\overset{O}{-C-}$ |
| 48 | 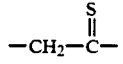 | H | —CH$_2$CH$_2$— | $\overset{OC_4H_9\text{-}n}{-CH-C-}\underset{O}{}$ |
| 49 | 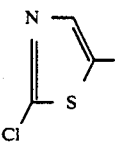 | H | —CH$_2$CH$_2$— | 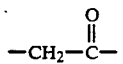 |

TABLE 1-continued

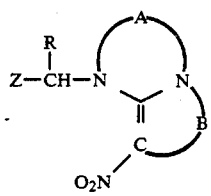

| Compound No. | Z | R | (Z—CHR—N side) A | (C side) B (N side) |
|---|---|---|---|---|
| 50 | 2-chloro-thiazol-5-yl | H | —CH$_2$CH$_2$— | —CH(SCH$_3$)—C(=O)— |
| 51 | pyridazin-4-yl | H | —CH$_2$CH$_2$— | —CH(OH)—C(=O)— |
| 52 | 6-chloro-pyridin-3-yl | H | —CH$_2$CH$_2$— | —C(OH)(C(CH$_3$)$_3$)—CH$_2$— |
| 53 | 6-chloro-pyridin-3-yl | H | —CH$_2$CH$_2$— | —C(=O)—CH$_2$— |
| 54 | 2-chloro-3-fluoro-pyridin-5-yl | H | —CH$_2$CH$_2$— | —C(=O)—CH$_2$— |
| 55 | 2-trifluoromethyl-thiazol-5-yl | H | —(CH$_2$)$_3$— | —C(=O)—CH$_2$— |
| 56 | 6-chloro-pyridin-3-yl | H | —(CH$_2$)$_3$— | —C(=NH)—CH$_2$— |
| 57 | 6-chloro-pyridin-3-yl | H | —CH$_2$CH$_2$— | —C(=O)—C(=O)— |
| 58 | 2-chloro-thiazol-5-yl | H | —(CH$_2$)$_3$— | —C(=O)—C(=O)— |
| 59 | 6-chloro-pyridin-3-yl | H | —CH$_2$CH$_2$— | —S—C(=O)— |

TABLE 1-continued
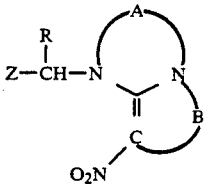
| Compound No. | Z | R | (Z—CHR—N side) A | (C side) B (N side) | |
|---|---|---|---|---|---|
| 60 | 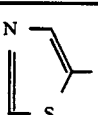 | H | —(CH$_2$)$_3$— |  | |
| 61 | 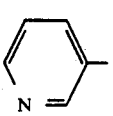 | H | —CH$_2$CH$_2$— |  | |
| 62 | 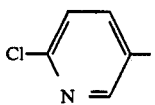 | H | —CH$_2$CH$_2$— |  | |
| 63 | 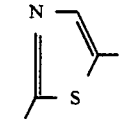 | H | —CH$_2$CH$_2$— | 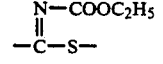 | mp. 176–180° C. |
| 64 | 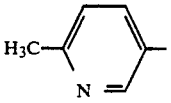 | H | —CH$_2$CH$_2$— | 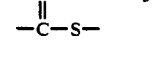 | |
| 65 | 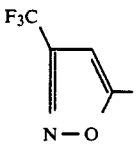 | H | —(CH$_2$)$_3$— | 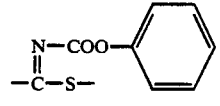 | |
| 66 | 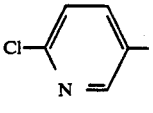 | H | —CH$_2$CH$_2$— | 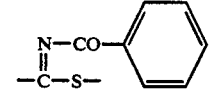 | |
| 67 | 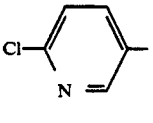 | H | —CH$_2$CH$_2$— | —CH=N— | |
| 68 | 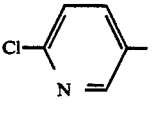 | H | —CH$_2$CH$_2$— |  | |
| 69 | 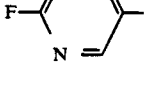 | H | —(CH$_2$)$_3$— |  | |

TABLE 1-continued

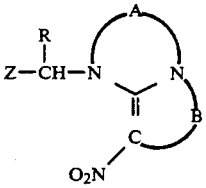

| Compound No. | Z | R | (Z—CH—N side) A | (C side) B (N side) |
|---|---|---|---|---|
| 70 | 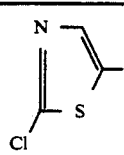 | H | —CH₂CH₂— | $\underset{\underset{}{-\text{C}=\text{N}-}}{\text{OC}_2\text{H}_5}$ |
| 71 | 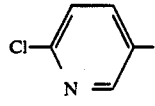 | H | —CH₂CH₂— | $-\underset{\|}{\overset{\text{O}}{\text{C}}}-\text{NH}-$ |
| 72 | 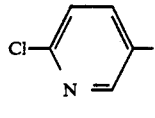 | H | —CH₂CH₂— | $-\underset{\|}{\overset{\text{O}}{\text{C}}}-\underset{\|}{\overset{\text{CH}_3}{\text{N}}}-$ |
| 73 | 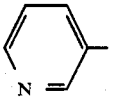 | H | —CH₂CH₂— | —N=N— |
| 74 | 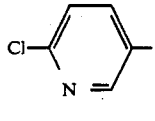 | H | —CH₂CH₂— | —N=N— |
| 75 | 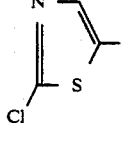 | H | —CH₂CH₂— | —N=N— |
| 76 | 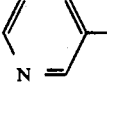 | H | —CH₂CH₂— | —CH₂CH₂CH₂— |
| 77 | 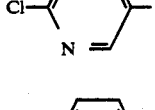 | H | —CH₂CH₂— | —CH₂CH₂CH₂— |
| 78 | 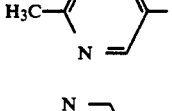 | H | —(CH₂)₃— | —CH₂CH₂CH₂— |
| 79 | 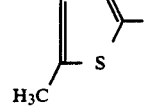 | H | —CH₂CH₂— | —CH₂CH₂CH₂— |

TABLE 1-continued

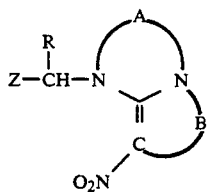

| Compound No. | Z | R | (Z—CHR—N side) A | (C side) B (N side) |
|---|---|---|---|---|
| 80 | 5-methylpyrazin-2-yl (H$_3$C-pyrazine) | H | —CH$_2$CH$_2$— | —CH$_2$C(CH$_3$)$_2$CH$_2$— |
| 81 | 6-chloropyridin-3-yl | H | —CH$_2$CH$_2$— | —CH=CH—CH$_2$— |
| 82 | 1,2,3-thiadiazol-5-yl | H | —(CH$_2$)$_3$— | —CH=CH—CH$_2$— |
| 83 | pyrimidin-5-yl | H | —CH$_2$CH$_2$— | —CH=CH—CH$_2$— |
| 84 | 6-chloropyridin-3-yl | H | —(CH$_2$)$_3$— | —CH$_2$CH$_2$C(=O)— |
| 85 | 6-methylpyridin-3-yl | H | —CH$_2$CH$_2$— | —CH$_2$CH(CH$_3$)C(=O)— |
| 86 | 2-chlorothiazol-5-yl | H | —CH$_2$CH$_2$— | —CH$_2$CH$_2$C(=O)— |
| 87 | pyridin-4-yl | H | —CH$_2$CH$_2$— | —CH=CH—C(=O)— |
| 88 | 6-fluoropyridin-3-yl | H | —CH$_2$CH$_2$— | —CH=CH—C(=O)— |
| 89 | 6-bromopyridin-3-yl | H | —(CH$_2$)$_3$— | —CH=CH—C(=O)— |

TABLE 1-continued

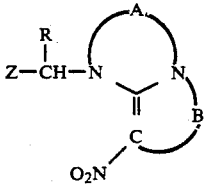

| Compound No. | Z | R | (Z—CH—N side) A with R | (C side) B (N side) |
|---|---|---|---|---|
| 90 | 3-chloro-isoxazol-5-yl (Cl, N—O) | H | —CH$_2$CH$_2$— | —CH=CH—C(=O)— |
| 91 | 6-chloropyridin-3-yl | H | —CH$_2$CH$_2$— | —CH(OC$_2$H$_5$)—CH$_2$—C(=O)— |
| 92 | pyridin-3-yl | H | —CH$_2$CH$_2$— | —CH$_2$—C(COOC$_2$H$_5$)—C(=O)— |
| 93 | 6-fluoropyridin-3-yl | H | —CH$_2$CH$_2$— | —CH(OCH$_3$)—CH(COOCH$_3$)—C(=O)— |
| 94 | 6-chloropyridin-3-yl | CH$_3$ | —CH$_2$CH$_2$— | —CH(SCH$_3$)—CH(COOC$_2$H$_5$)—C(=O)— |
| 95 | 6-chloropyridin-3-yl | H | —CH$_2$CH$_2$— | —CH(OCH$_3$)—CH(CN)—C(=O)— |
| 96 | 6-chloropyridin-3-yl | H | —CH$_2$CH$_2$— | —CH(COOC$_3$H$_7$-iso)—CH$_2$—C(=O)— |
| 97 | 5,6-dichloropyridin-3-yl | H | —CH$_2$CH$_2$— | —C(COOCH$_3$)=CH—C(=O)— |
| 98 | 6-bromopyridin-3-yl | H | —(CH$_2$)$_3$— | —C(COOC$_2$H$_5$)=CH—C(=O)— |
| 99 | 3-methyl-isoxazol-5-yl (H$_3$C, N—O) | H | —CH$_2$CH$_2$— | —C(COOC$_2$H$_5$)=CH—C(=O)— |

TABLE 1-continued
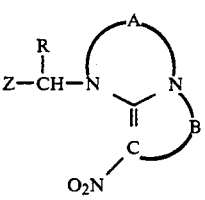
| Compound No. | Z | R | (Z—CH—N side) A | (C side) B (N side) |
|---|---|---|---|---|
| 100 | 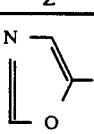 | H | —CH₂CH₂— | 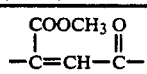 |
| 101 | 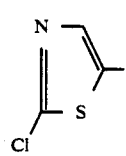 | H | —CH₂CH₂— | 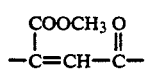 |
| 102 | 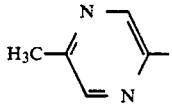 | H | —CH₂CH₂— | 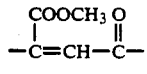 |
| 103 | 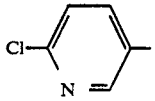 | H | —(CH₂)₃— | 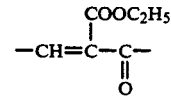 |
| 104 | 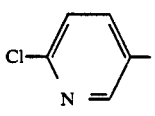 | H | —CH₂CH₂— | 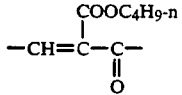 |
| 105 | 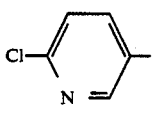 | H | —CH₂CH₂— | 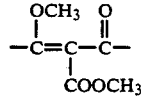 |
| 106 | 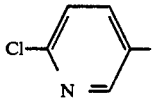 | H | —CH₂CH₂— | 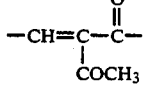 |
| 107 | 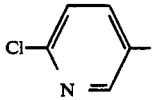 | H | —CH₂CH₂— | 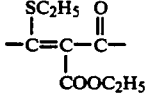 |
| 108 | 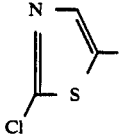 | H | —CH₂CH₂— | 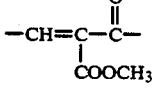 |
| 109 | 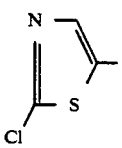 | H | —(CH₂)₃— | 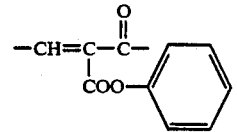 |

TABLE 1-continued

| Compound No. | Z | R | (Z—CHR—N side) A | (C side) B (N side) |
|---|---|---|---|---|
| 110 | 2-chloro-thiazol-5-yl | H | —CH₂CH₂— | —CH=C(CN)—C(=O)— |
| 111 | 6-chloro-pyridin-3-yl | H | —CH₂CH₂— | —CH₂—C(=O)—CH₂— |
| 112 | 6-chloro-pyridin-3-yl | H | —CH₂CH₂— | —C(=O)—CH₂—C(=O)— |
| 113 | pyridin-3-yl | H | —CH₂CH₂— | —C(=O)—C(CH₃)₂—C(=O)— |
| 114 | 6-fluoro-pyridin-3-yl | H | —CH₂CH₂— | —C(=NH)—CH₂CH₂— |
| 115 | 6-chloro-pyridin-3-yl | H | —CH₂CH₂— | —C(=NH)—CH₂CH₂— |
| 116 | 2-chloro-thiazol-5-yl | H | —CH₂CH₂— | —C(=NH)—CH₂CH₂— |
| 117 | 6-chloro-pyridin-3-yl | H | —CH₂CH₂— | —C(=NH)—CH₂—C(=O)— |
| 118 | 6-chloro-pyridin-3-yl | H | —CH₂CH₂— | —C(OH)(n-C₄H₉)—N(Ph)—C(=O)— |

TABLE 1-continued

| Compound No. | Z | R | (Z—CH(R)—N side) A | (C side) B (N side) | |
|---|---|---|---|---|---|
| 119 | 6-chloropyridin-3-yl | H | —CH₂CH₂— | $-\overset{HO}{\underset{\underset{C_6H_5}{|}}{C}}-\overset{C_4H_9\text{-}n}{\underset{}{N}}-\overset{}{\underset{}{C}}-$ with phenyl | |
| 120 | 6-chloropyridin-3-yl | H | —CH₂CH₂— | $-\overset{}{\underset{CHCH_3}{\overset{\parallel}{C}}}-\overset{CH_2C_6H_5}{\underset{}{N}}-\overset{O}{\underset{}{C}}-$ | |
| 121 | 2-chlorothiazol-5-yl | H | —CH₂CH₂— | $-\overset{}{\underset{CH_2}{\overset{\parallel}{C}}}-\overset{CH_3}{\underset{}{N}}-\overset{O}{\underset{}{C}}-$ | |
| 122 | 6-chloropyridin-3-yl | H | —CH₂CH₂— | —C(CH₃)₂—NH—C(=O)— | |
| 123 | 6-fluoropyridin-3-yl | H | —CH₂CH₂— | —C(=O)—NH—C(=O)— | |
| 124 | 5,6-dichloropyridin-3-yl | H | —(CH₂)₃— | —C(=O)—NH—C(=O)— | mp. 196–200° C. |
| 125 | 3-chloroisoxazol-5-yl | H | —CH₂CH₂— | —C(=O)—NH—C(=O)— | |
| 126 | 2-chlorothiazol-5-yl | H | —CH₂CH₂— | —C(=S)—NH—C(=O)— | mp. >300° C. |
| 127 | 6-chloropyridazin-3-yl | H | —CH₂CH₂— | —C(=O)—NH—C(=O)— | |

TABLE 1-continued
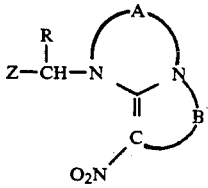
| Compound No. | Z | R | (Z—CH—N side) A | (C side) B (N side) |
|---|---|---|---|---|
| 128 | 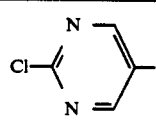 | H | —CH₂CH₂— | 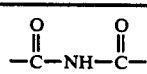 |
| 129 | 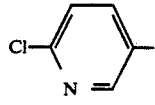 | H | —CH₂CH₂— | 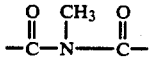 |
| 130 | 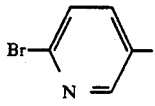 | H | —CH₂CH₂— | 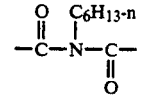 |
| 131 | 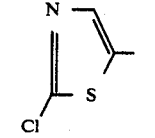 | H | —CH₂CH₂— | 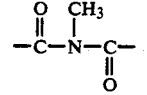 |
| 132 | 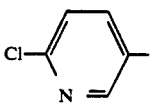 | H | —CH₂CH₂— | 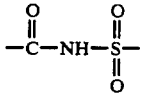 |
| 133 | 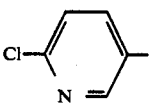 | H | —CH₂CH₂— | 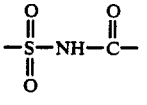 |
| 134 | 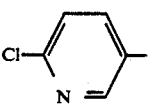 | H | —CH₂CH₂— | —CH₂—O—CH₂— |
| 135 | 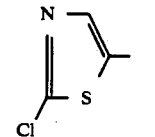 | H | —CH₂CH₂— | —CH₂—O—CH₂— |
| 136 | 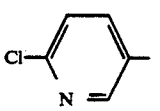 | H | —CH₂CH₂— | —CH₂—S—CH₂— |
| 137 | 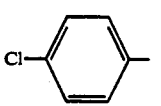 | H | —CH₂CH₂— | —CH=CH— |

TABLE 1-continued $$\text{Z}-\underset{R}{\overset{|}{CH}}-N\underset{\underset{O_2N}{\overset{\parallel}{C}}}{\overset{A}{\diagdown}}N\diagup B$$

| Compound No. | Z | R | (Z—CHR—N side) A | (C side) B (N side) |
|---|---|---|---|---|
| 138 | 4-Br-C6H4- | H | —CH₂CH₂— | —C(C₄H₉-tert)=CH— |
| 139 | 3-CN-C6H4- | H | —CH₂CH₂— | —CH=CH— |
| 140 | 4-F-C6H4- | H | —CH₂CH₂— | —CH₂—C(=O)— |
| 141 | 3-Cl-4-F-C6H3- | H | —(CH₂)₃— | —CH₂—C(=O)— |
| 142 | 3,4-Cl₂-C6H3- | H | —CH₂CH₂— | —CH₂—C(=O)— |
| 143 | 3-NO₂-C6H4- | H | —CH₂CH₂— | —CH(OH)—C(=O)— |
| 144 | 3-CN-C6H4- | H | —CH₂CH₂— | —CH(OH)—C(=O)— |
| 145 | 4-Cl-C6H4- | H | —CH₂CH₂— | —C(=O)—S— |
| 146 | 3-CN-C6H4- | H | —CH₂CH₂— | —C(=O)—S— |

TABLE 1-continued

[Structure diagram showing Z—CH(R)—N connected in a ring system with A, B, C, and O₂N substituents]

| Compound No. | Z | R | (Z—CH(R)—N side) A | (C side) B (N side) | |
|---|---|---|---|---|---|
| 147 | 4-Cl-C₆H₄— | H | —(CH₂)₃— | —C(=N-COOC₂H₅)—S— | |
| 148 | 3,4-Cl₂-C₆H₃— | H | —CH₂CH₂— | —C(=N-COO-C₆H₅)—S— | |
| 149 | 3-CN-C₆H₄— | H | —CH₂CH₂— | —C(OC₂H₅)=N— | |
| 150 | 4-Cl-C₆H₄— | H | —CH₂CH₂— | —C(=O)—NH— | |
| 151 | 3-CN-C₆H₄— | H | —(CH₂)₃— | —N=N— | |
| 152 | 4-Br-C₆H₄— | H | —CH₂CH₂— | —CH=CH— | |
| 153 | 4-Cl-C₆H₄— | H | —CH₂CH₂— | —CH₂CH₂C(=O)— | |
| 154 | 4-CN-C₆H₄— | H | —CH₂CH₂— | —CH=CH—C(=O)— | |
| 155 | 3-CN-C₆H₄— | H | —CH₂CH₂— | —C(COOCH₃)=CH—C(=O)— | mp. 219–222° C. |
| 156 | 3,4-Cl₂-C₆H₃— | H | —CH₂CH₂— | —CH=CH—C(=O)— | |

TABLE 1-continued

Structure:
Z—CH(R)—N—A—N=C(—NO2)—B (cyclic)

| Compound No. | Z | R | (Z—CH(R)—N side) A | (C side) B (N side) |
|---|---|---|---|---|
| 157 | 4-Cl-phenyl | H | —(CH2)3— | NH‖—C—CH2CH2— |
| 158 | 3-CN-phenyl | H | —CH2CH2— | —C(=O)—NH—C(=O)— |
| 159 | 2-Cl, 4-CN-phenyl (Cl and CN on phenyl) | H | —CH2CH2— | —C(=O)—NH—C(=O)— |

Biotest Examples:

Control Compounds:

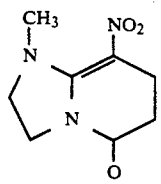

C-1 (described in "Chemische Berichte", 1968, Vol. 119, pp. 2208-2219)

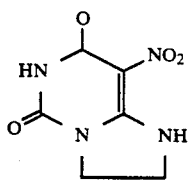

C-2 (described in "Heterocycles", 1980, Vol. 15, p. 437)

Example 4

Biotest carried out against *Nephotettix cinctipceps* exhibiting resistance to oranophosphorus series insecticides Preparation of test formulation: Solvent: 3 parts by weight of xylene Emulsifier: 1 part by weight of polyoxyethylene-alkylphenyl-ether To prepare a suitable formulation of an active compound, 1 part by weight of the active compound was mixed with the above amount of the solvent containing the above amount of the emulsifier, and the mixture was diluted with water to the predetermined concentration.

Test method:

Use was made of a plurality of pots each having a diameter of 12 cm in which were planted rice plant seedlings each having a height of about 10 cm.

Onto each potted rice-plant seedling was sprayed 10 ml of an aqueous solution of the above prepared active compound having the predetermined concentration.

After the sprayed solution was dried up, each of the pots was covered with a screen having a diameter of 7 cm and a height of 14 cm, in which 30 pieces of female adults of Nephotettix cincticeps exhibiting resistance to organophosphorus-series insecticides were released, then each pot was placed in a constant temperature chamber. Two days after, the number of the killed insects was counted to obtain the mortality rate of the insects.

The test results were determined on an average basis, they are shown in Table 2.

TABLE 2

| Compound No. | Concentration of active compound in ppm | Insect mortality in % |
|---|---|---|
| 1 | 200 | 100 |
| 4 | 200 | 100 |
| 6 | 200 | 100 |
| 8 | 200 | 100 |
| 9 | 200 | 100 |
| Comparison compounds | | |
| C-1 | 1000 | 20 |
| C-2 | 1000 | 12 |

Example 5

Biotest carried out against *Myzus persicae* exhibiting resistance to organophosphorus and carbamate-series insecticides Test method:

Onto eggplant seedlings (black long eggplant) each having a height of 20 cm and planted on an unglazed pot having a diameter of 15 cm per one seedling, 200 pieces of grown *Myzus persicae* having resistance against organophosphorus and carbamate-series insecticides were inoculated. One day after the inoculation, an aqueous solution having a predetermined concentration of the active compound, which had been prepared according to the procedure similar to Example 4, was sprayed onto the seedlings with a sufficient dosage.

The above-mentioned test was carried out for each of the below-indicated active compounds with the indicated concentration dosages. After the spraying of the insecticidal solution, the seedlings in the pot for each test were allowed to stand for 24 hours in a green house kept at a temperature of 28° C. and, thereafter, the mortality rate of the insects was determined for each test. The same test was repeated twice for the purpose of obtaining an accurate mortality rate determination, the result of which is shown in the following Table 3;

TABLE 3

| Compound No. | Concentration of active compound, ppm | Insect mortality, % |
|---|---|---|
| 1 | 200 | 100 |
| 4 | 200 | 100 |
| 6 | 200 | 100 |
| 8 | 200 | 100 |
| 9 | 200 | 100 |
| Comparison compounds | | |
| C-1 | 1000 | 0 |
| C-2 | 1000 | 0 |

It will be appreciated that the instant specification and claims are set forth by way of illustration and not limitation, and that various modifications and changes may be made without departing from the spirit and scope of the present invention.

What is claimed is:

1. A nitro-substituted heterocyclic compound of the formula (I)

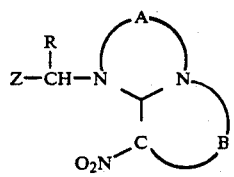

wherein
R is hydrogen or $C_1$-$C_4$ alkyl,
Z is $C_6$-$C_{10}$ aryl, or a 5 to 6-membered heterocyclic group containing 1 to 2 hetero atoms selected from the group consisting of O, S and N, at least one of which is a nitrogen atom, and said aryl or heterocyclic group is unsubstituted or substituted respectively by one or two members independently selected from the group consisting of halogen, $C_1$-$C_4$ alkyl, $C_1$-$C_4$ alkoxy, $C_1$-$C_4$ haloalkyl, $C_1$-$C_4$ alkylthio, $C_1$-$C_4$ haloalkoxy, $C_1$-$C_4$ haloalkylthio, nitro, and cyano,
A is propylene, which is unsubstituted or substituted by methyl, and
B stands for 3 members, two of which are carbon and one of which is a nitrogen atom located between the two carbon atoms, at least one of said carbon atoms being substituted by a keto group, another of said carbon atoms and the nitrogen atom being unsubstituted or substituted by at least one substituent selected from the group consisting of halogen, $C_1$-$C_6$ alkyl, $C_1$-$C_4$ alkoxy, alkoxycarbonyl having 1 to 4 carbon atoms in the alkoxy part, unsubstituted or substituted $C_6$-$C_{10}$ aryl, keto, imino, phenoxy, $C_1$-$C_4$ alkoxythio, alkoxycarbonylimino having 1 to 4 carbon atoms in the alkoxy part, phenoxycarbonylimino, benzoylimino, benzyl, cyano, thioketo, hydroxy and $C_1$-$C_2$ alkylidene.

2. A nitro-substituted heterocyclic compound according to claim 1, wherein
R is hydrogen, or methyl,
Z is phenyl, or a 5 to 6-membered heterocyclic group containing 1 to 2 hetero atoms selected from the group consisting of O, S and N, at least one of which is a nitrogen atom, and said phenyl and heterocyclic group are unsubstituted or substituted by one or two substituents selected from the group consisting of fluorine, chlorine, bromine, methyl, ethyl, methoxy, trifluoromethyl, methylthio, trifluoromethoxy, trifluoromethylthio, nitro and cyano,
A is propylene which may be substituted by methyl, and
B stands for 3 members two of which are carbon and one of which is a nitrogen atom located between the two carbon atoms, at least one of said carbon atoms being substituted by a keto group, another of said carbon atoms and the nitrogen atom being unsubstituted or substituted by at least one substituent selected from the group consisting of halogen, $C_1$-$C_6$ alkyl, $C_1$-$C_4$ alkoxy, alkoxycarbonyl having 1 to 4 carbon atoms in the alkoxy part, unsubstituted or substituted $C_6$-$C_{10}$ aryl, keto, imino, phenoxy, $C_1$-$C_4$ alkoxythio, alkoxycarbonylimino having 1 to 4 carbon atoms in the alkoxy part, phenoxycarbonylimino, benzoylimino, benzyl, cyano, thioketo, hydroxy and $C_1$-$C_2$ alkylidene.

3. A pesticidal composition for combating arthropod pests comprising a pesticidally effective amount of at least one nitro-substituted heterocyclic compound according to claim 1 in admixture with a diluent.

4. A method for combating harmful arthropod pests comprising applying to said pests and/or their habitat a pesticidally effective amount of at least one nitro-substituted heterocyclic compound according to claim 1.

* * * * *